United States Patent
Bang et al.

(10) Patent No.: US 8,753,287 B2
(45) Date of Patent: Jun. 17, 2014

(54) HEARING TEST METHOD AND APPARATUS

(75) Inventors: Kyoung Ho Bang, Seoul (KR); Sang Ki Kang, Gyeonggi-do (KR); Yang Su Kim, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 281 days.

(21) Appl. No.: 13/110,079

(22) Filed: May 18, 2011

(65) Prior Publication Data
US 2012/0157876 A1     Jun. 21, 2012

(30) Foreign Application Priority Data
Dec. 21, 2010 (KR) .................. 10-2010-0131122

(51) Int. Cl.
*A61B 5/00* (2006.01)
(52) U.S. Cl.
USPC .......................................................... 600/559

(58) Field of Classification Search
USPC .......................................................... 600/559
See application file for complete search history.

(56) References Cited

U.S. PATENT DOCUMENTS
2010/0137739 A1    6/2010   Lee et al.

*Primary Examiner* — Brian Szmal
(74) *Attorney, Agent, or Firm* — Cha & Reiter, LLC (57) ABSTRACT

A hearing test method and apparatus are provided for improving a measuring accuracy and a test speed in finding the auditory threshold that is the audibility limit of discriminating a sound. In the method, after outputting a test sound relevant to a selected test frequency and a selected test sound pressure, the apparatus determines whether a user hears the test sound, then the test sound pressure zone is divided into an auditory threshold presence region and an auditory threshold absence region according to the result of determination. Thereafter, the test sound pressure zone is redefined using the auditory threshold presence region and this process of hearing test is repeated using the redefined test sound pressure zone to finally determine an auditory threshold for the selected test frequency.

18 Claims, 10 Drawing Sheets

HEARING TEST METHOD AND APPARATUS

CLAIM OF PRIORITY

This application makes reference to and claims all benefits from an application entitled filed in the Korean Intellectual Property Office on Dec. 21, 2010 and there duly assigned Serial No. 10-2010-0131122, the contents of which are hereby incorporated by reference.

BACKGROUND OF THE INVENTION

1. Field of the Invention

The present invention relates generally to a hearing test technology and, more particularly, to a hearing test method and apparatus for improving a measurement accuracy and a test speed in finding the auditory threshold used to discriminate a sound.

2. Description of the Related Art

The number of persons who have difficulty in hearing is increasing every year. Especially, noise-induced hearing loss is rising rapidly. In addition, age-related or any other cause-induced hearing loss keeps on growing. Being exposed to everyday noises, such as listening to very loud music over many years, may have contributed to many hearing loss.

FIGS. 1 to 5 illustrate two conventional hearing test methods. One of them is based on a descending approach, and the other is based on an ascending approach.

Figure 1:
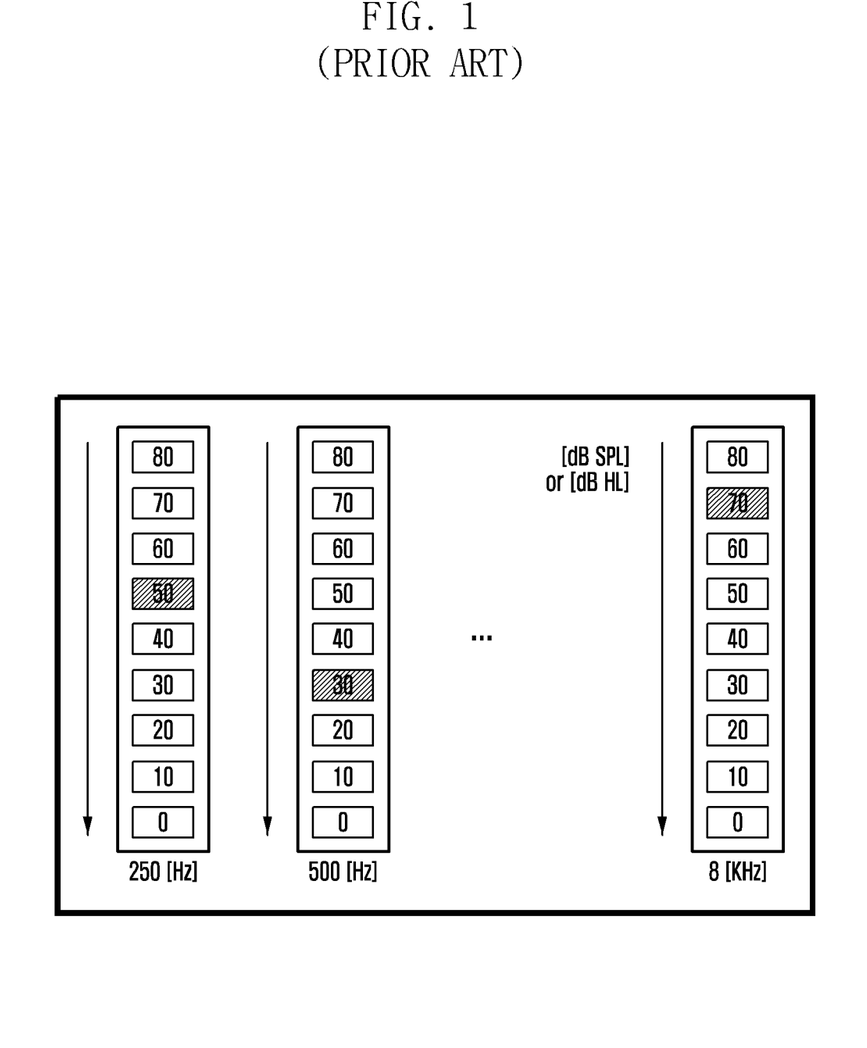
FIG. 1 is a view illustrating a conventional hearing test method based on a descending approach.
Figure 2:
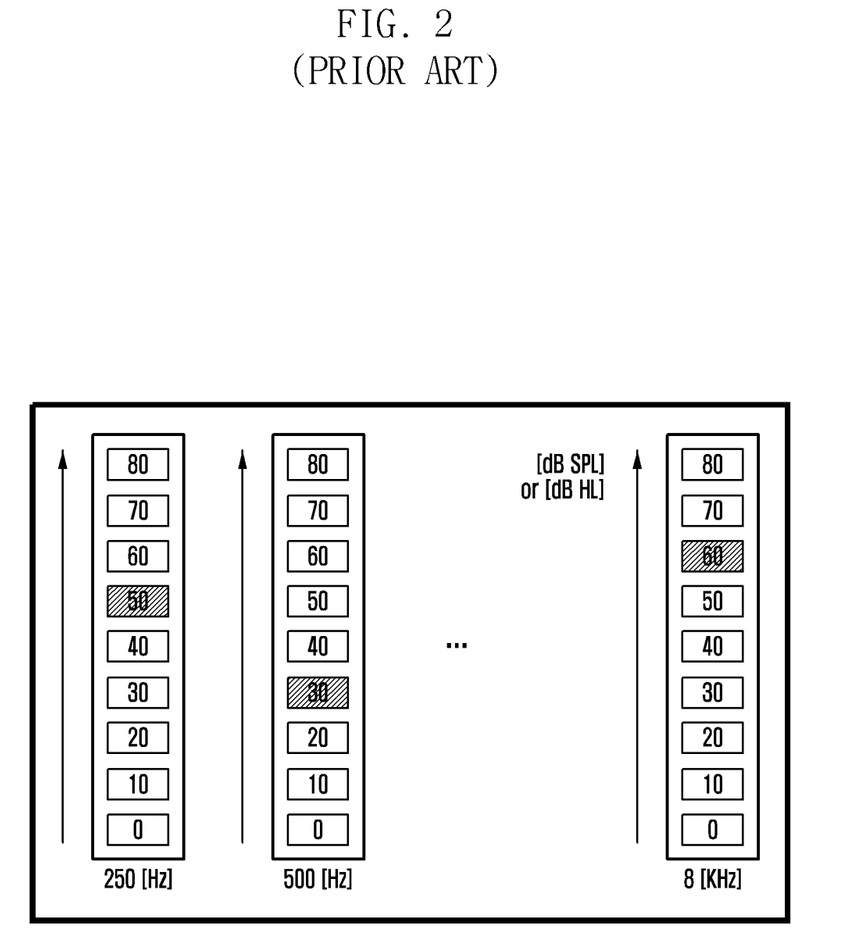
FIG. 2 is a view illustrating a conventional hearing test method based on an ascending approach.

As shown in FIG. 1, the descending approach is to measure a person's sense of hearing by gradually decreasing a test sound from a higher level (intensity) at different frequencies such as 250 Hz, 500 Hz, 1 kHz, 2 kHz, 4 kHz and 8 kHz. In contrast, as shown in FIG. 2, the ascending approach gradually increases a test sound from a lower level at various frequencies. Normally the descending approach yields a lower result of the auditory threshold by 5-10 dB than the ascending approach. According to such conventional hearing test methods, process of selecting a frequency, outputting a test sound for a selected frequency and checking a response or not are sequentially performed.

Figure 3:
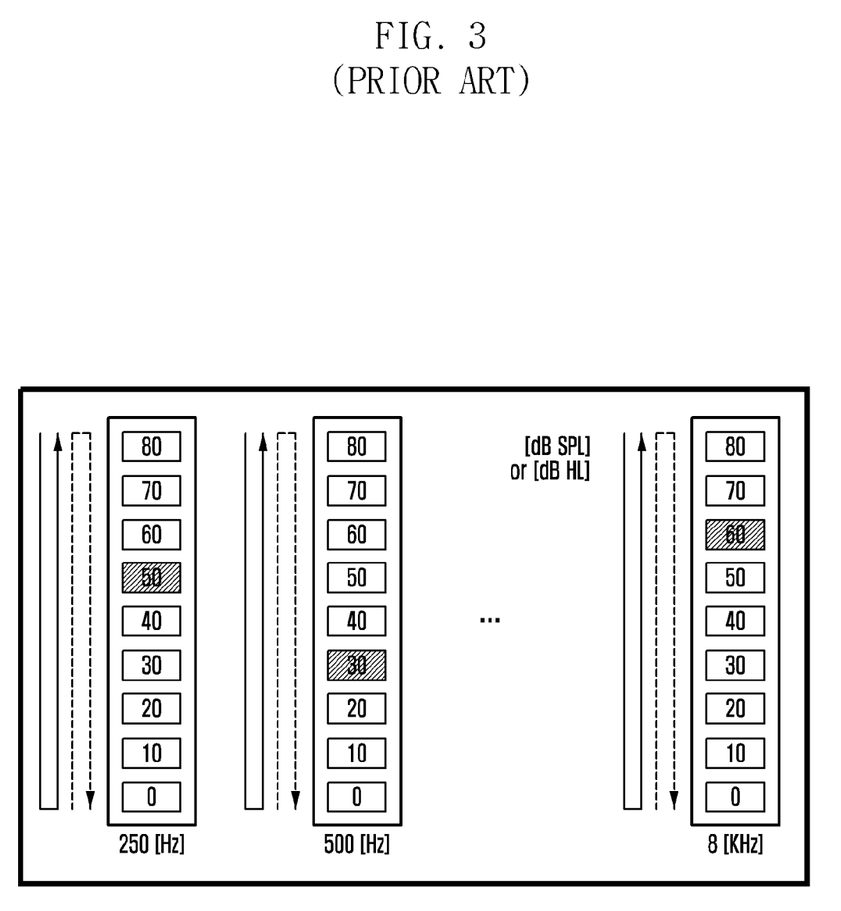
FIG. 3 is a view illustrating a conventional hearing test method based on a mixed approach.
Figure 4:
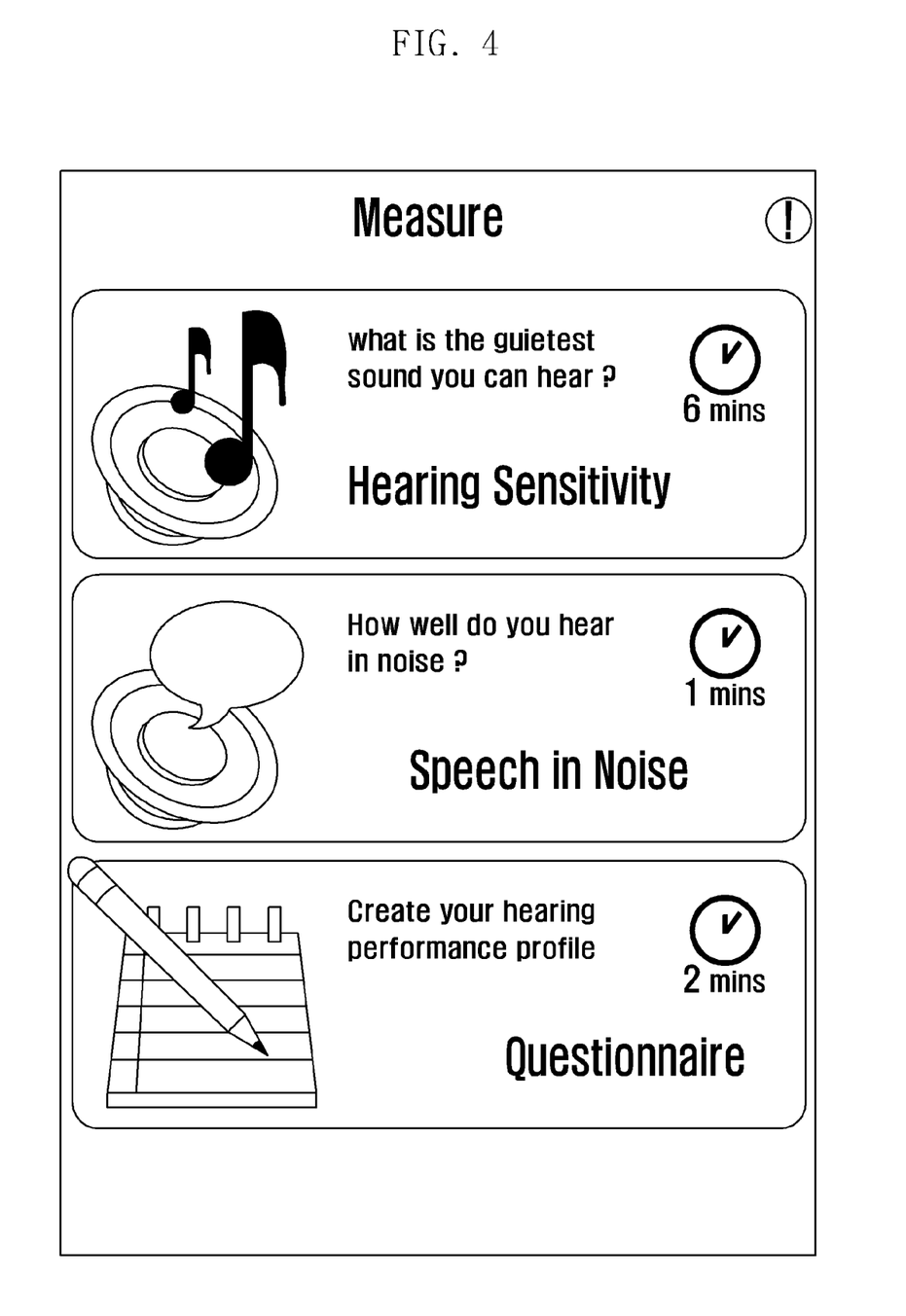
FIG. 4 is an initial screen of a conventional hearing test application based on a mixed approach.

In another conventional hearing test method, a method based on a mixed approach is known in the art. Referring to FIG. 3, the mixed approach is to find an initial auditory threshold through the ascending approach and then determine the final auditory threshold through the descending approach, or vice versa. Referring to FIG. 4, a related application 'uHear' registered in the application store operated by Apple Inc. is an example of using the mixed approach of ascent after descent.

Figure 5:
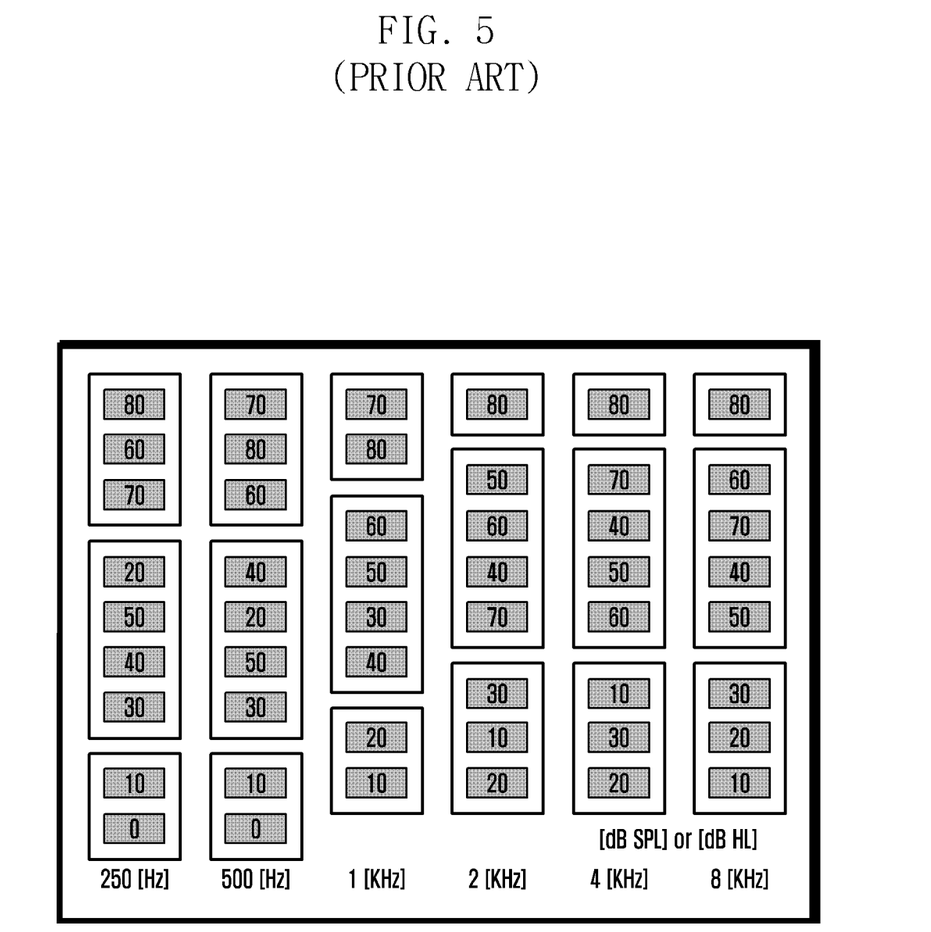
FIG. 5 is a view illustrating a conventional hearing test method based on a grouping approach.

In order to improve a test speed of the descending or ascending approach, still another conventional hearing test method is disclosed in the Korean Patent Publication No. 2010-22880 (US Publication 20100137739). Briefly, as shown in FIG. 5, this method is based on a grouping approach that uses two or more test sound sets. The grouping approach is to output some sets of test sounds and receive a user's response regarding how many test sounds could be heard.

Among the above-discussed conventional methods, the descending approach and the ascending approach are designed offer all sound pressure levels up to the auditory threshold for each frequency to a user. Therefore, a test duration is much longer, and also there is a difference in the auditory threshold between the descending and ascending approaches.

In case of the mixed approach, the required test duration nearly double when compared with the descending or ascending approach which in turn lowers a user's attention span. Further, ascent or descent by a uniform difference in sound pressure during test may allow a user to predict the next test sound and thus create an illusion as if he or she had heard a sound.

In case of the grouping approach, a test duration is relatively shorted compared to other approaches. However, since all test sounds have to be heard, it has the same drawbacks of lowering a user's attention span. Also, since the test duration is varied according to a region of the auditory threshold, there is a possibility that a difference in test accuracy will be caused due to variation in test concentration.

Accordingly, there is a need to improve the way to assess one's hearing.

BRIEF SUMMARY OF THE INVENTION

Accordingly, the present invention is to address the above-mentioned problems and/or disadvantages and to offer at least the advantages described below.

An aspect of the present invention is to provide a hearing test method and apparatus that can exactly and rapidly find the auditory threshold by gradually narrowing an auditory threshold presence probability space through a binary search approach.

Another aspect of the present invention is to provide a hearing test which includes: selecting a test frequency among a plurality of frequencies for a hearing test; selecting a test sound pressure in a test sound pressure zone for the selected test frequency; outputting a test sound relevant to the selected test frequency and the selected test sound pressure; determining whether a user hears the test sound; dividing the test sound pressure zone into an auditory threshold presence region and an auditory threshold absence region according to the result of determination and then redefining the test sound pressure zone by using the auditory threshold presence region; and determining an auditory threshold for the selected test frequency through a repeat from the selecting of the test frequency to the redefining of the test sound pressure zone.

In the embodiment, the redefining of the test sound pressure zone may include: if a user succeeds in hearing the test sound, determining a region below the selected test sound pressure as the auditory threshold presence region; and if a user fails to hear the test sound, determining a region above the selected test sound pressure as the auditory threshold presence region. Also, the auditory threshold presence region may be determined as the auditory threshold if being equal to or smaller than a predetermined minimum scope, and may be used to redefine the test sound pressure zone if being greater than the minimum scope. Further, the selected test sound pressure may be a middle point in the test sound pressure zone. Further the test frequency may be randomly selected among the plurality of frequencies for the hearing test. Further, the order of a random selection for the frequencies may be fixed in advance before the selecting of the test frequency.

Another aspect of the present invention is to provide a hearing test method includes: a pre-test for defining a test sound pressure zone for each of a plurality of frequencies for a hearing test; and a main test for finding an auditory threshold for each of the plurality of frequencies, wherein the main test includes: selecting a test frequency among the plurality of frequencies; selecting a test sound pressure in the test sound pressure zone for the selected test frequency; outputting a test sound relevant to the selected test frequency and the selected test sound pressure; determining whether a user hears the test sound; dividing the test sound pressure zone into an auditory threshold presence region and an auditory threshold absence region according to the result of determination and then redefining the test sound pressure zone by using the auditory threshold presence region; and determining the auditory threshold for the selected test frequency through a repeat from the selecting of the test frequency to the redefining of the test sound pressure zone.

In the embodiment, the test frequency in the main test may be randomly selected among the plurality of frequencies for the hearing test. Also, the main test may further include selecting other test frequency after the determining of the auditory threshold for the selected test frequency. Further, the selecting of the test frequency in the main test may include randomly selecting the test frequency among the rest frequencies other than the frequencies for which the auditory thresholds are determined.

According to yet another aspect of the present invention, a hearing test apparatus includes: an input unit configured to receive a user's response to a test sound; a frequency selection unit configured to select a test frequency among a plurality of frequencies for a hearing test; a sound pressure selection unit configured to select a test sound pressure in a test sound pressure zone for the selected test frequency; a test sound output unit configured to output the test sound relevant to the selected test frequency and the selected test sound pressure; and a test processing unit configured to determine whether a user hears the test sound, to divide the test sound pressure zone into an auditory threshold presence region and an auditory threshold absence region, to redefine the test sound pressure zone by using the auditory threshold presence region, and to determine an auditory threshold for the selected test frequency through a repeated redefining of the test sound pressure zone.

In the embodiment, the test processing unit may be further configured to determine a region below the selected test sound pressure as the auditory threshold presence region if a user succeeds in hearing the test sound. Also, the test processing unit may be further configured to determine a region above the selected test sound pressure as the auditory threshold presence region if a user fails to hear the test sound. Further, the test processing unit may be further configured to determine the auditory threshold presence region as the auditory threshold if the auditory threshold presence region is equal to or smaller than a predetermined minimum scope. Further, the test processing unit may be further configured to use the auditory threshold presence region to redefine the test sound pressure zone if the auditory threshold presence region is greater than the minimum scope. Further, the sound pressure selection unit may be further configured to select a middle point in the test sound pressure zone as the test sound pressure. Further, the sound pressure selection unit may be further configured to randomly select the test frequency among the plurality of frequencies for the hearing test, and further comprise a test data storage unit configured to store the auditory threshold.

The present invention adopts an approach that estimates the auditory threshold by reducing a region having a possibility of presence of the auditory threshold in units of $2^{-N}$ (N=1, 2, 3, ...). Namely, the invention outputs only some frequencies adjacent in probability to the auditory threshold, instead of outputting all frequencies, thus reducing a test time in comparison with conventional techniques. Therefore, the invention not only improves a user's attention, but also increases test accuracy.

Additionally, according to the present invention, a sound pressure of a test sound is random without ascending or descending by a uniform size. Also, a test frequency can be randomly selected. Therefore, this invention further increases test accuracy by preventing a prediction for the next test sound.

Other aspects, advantages, and salient features of the invention will become apparent to those skilled in the art from the following detailed description, which, taken in conjunction with the annexed drawings, discloses exemplary embodiments of the invention.

DETAILED DESCRIPTION OF THE INVENTION

Exemplary, non-limiting embodiments of the present invention will now be described more fully with reference to the accompanying drawings. This invention may, however, be embodied in many different forms and should not be construed as limited to the exemplary embodiments set forth herein. Rather, the disclosed embodiments are provided so that this disclosure will be thorough and complete, and will fully convey the scope of the invention to those skilled in the art. The principles and features of this invention may be employed in varied and numerous embodiments without departing from the scope of the invention.

For the purposes of clarity and simplicity, well known or widely used techniques, elements, structures, and processes may not be described or illustrated in detail to avoid obscuring the essence of the present invention. Although the drawings represent exemplary embodiments of the invention, the drawings are not necessarily to scale and certain features may be exaggerated or omitted in order to better illustrate and explain the present invention.

Among terms set forth herein, 'a test sound' refers to a sound produced by or stored in a hearing test apparatus for testing a user's hearing and is outputted through various audio output means. 'A test sound pressure' refers to a sound pressure level in dBHL units into which a test sound is converted. 'A test frequency' refers to the frequency of a test sound. 'A test sound pressure zone' refers to the range of a test sound pressure that can be applied to a test sound. Namely, any test sound may have its sound pressure level selected within a test sound pressure zone.

Figure 6:
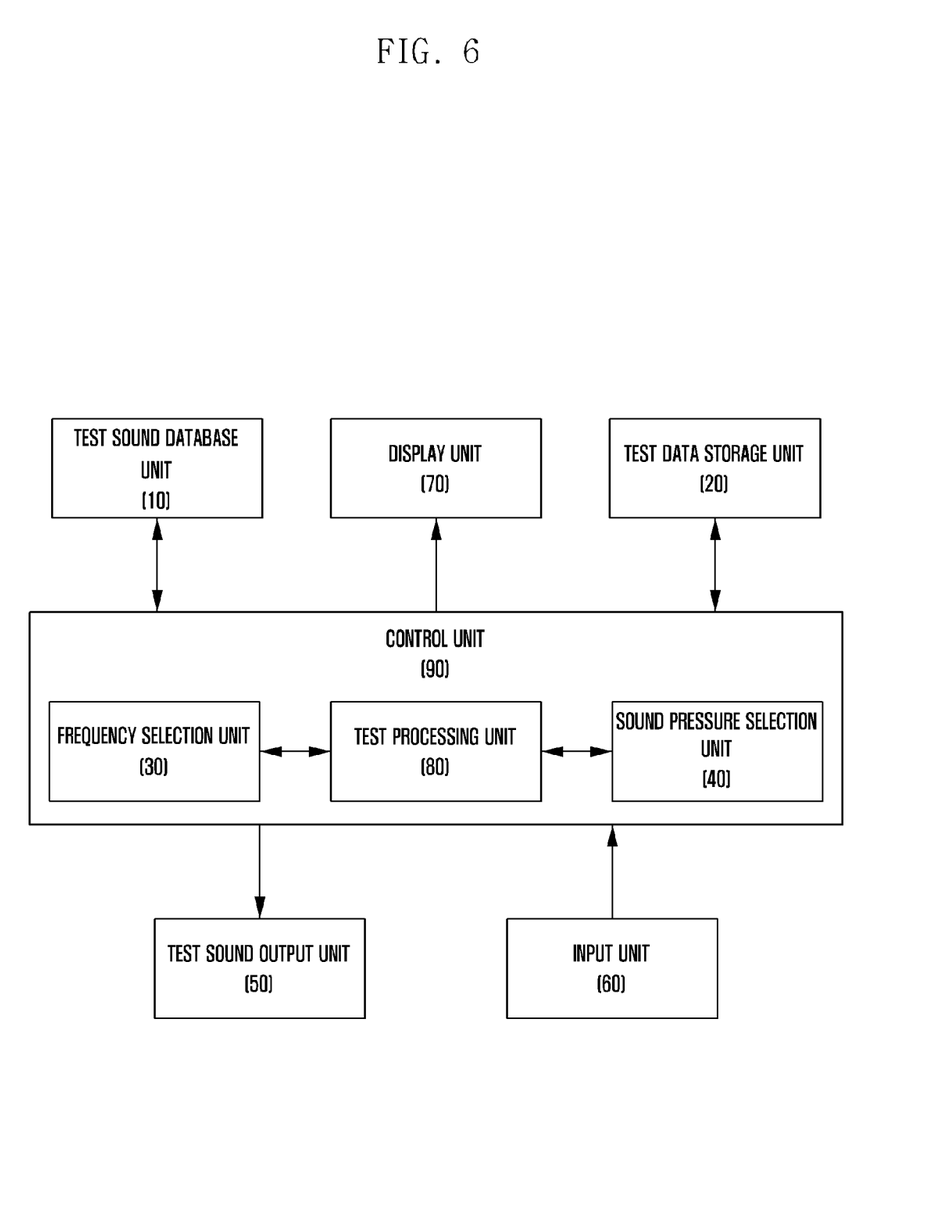
FIG. 6 is a block diagram illustrating the configuration of a hearing test apparatus in accordance with an exemplary embodiment of the present invention.

FIG. 6 is a block diagram illustrating the configuration of a hearing test apparatus in accordance with an exemplary embodiment of the present invention.

As shown in FIG. 6, the hearing test apparatus according to an embodiment of this invention may include a test sound database unit 10, a test data storage unit 20, a test sound output unit 50, an input unit 60, a display unit 70, and a control unit 90.

The test sound database unit 10 stores test sounds necessary for a hearing test. Test sounds are sorted by frequency and sound pressure. If there are six frequencies such as 250 Hz, 500 Hz, 1 kHz, 2 kHz, 4 kHz and 8 kHz, and if there are eight sound pressures levels at 10 dB intervals from 0 to 80 dB, the number of test sounds stored in the test sound database unit 10 is forty eight in total. It should be noted that six test frequencies and eight test sound pressures are exemplary only and not to be considered as a limitation of this invention. Any audible frequency level or range may be used for the test frequency and also any sound pressure level more than 80 dB may be used for the test sound pressure. Further, an interval between text sound pressures may be not 10 dB but 5 dB, for example.

The test data storage unit 20 stores user hearing state information obtained by means of a hearing test. Additionally, the test data storage unit 20 may deliver the hearing state information to the control unit 90 or to any application.

The test sound output unit 50 outputs a specific test sound relevant to a test frequency selected by a frequency selection unit 30 and a test sound pressure selected by a sound pressure selection unit 40. The test sound output unit 50 may have a converter that converts a digital signal, i.e., a test sound inputted from the control unit 90, into an analog signal and then outputs it to a speaker, receiver or earphone.

The input unit 60 receives a user's response to a test sound outputted through the test sound output unit 50 and then delivers it to the control unit 90. The input unit 60 may include a keypad, a touch pad, a touch screen, and a microphone.

The control unit 90 repeatedly performs a binary search process and thereby determines the auditory thresholds of some frequencies selected for a hearing test. The control unit 90 may include the frequency selection unit 30, the sound pressure selection unit 40, and a test processing unit 80.

The frequency selection unit 30 selects a test frequency among a plurality of frequencies for a hearing test. Namely, the frequency selection unit 30 selects the frequency of a test sound to be outputted from the test sound output unit 50. Here, a test frequency may be randomly selected.

The sound pressure selection unit 40 retrieves a test sound pressure zone assigned to each test frequency from the test data storage unit 20 and then selects a test sound pressure. For instance, if the test sound pressure zone of 1 kHz is defined as [0 dB, 80 dB], the sound pressure selection unit 40 selects an average value 40 dB as a test sound pressure.

The test processing unit 80 retrieves a test sound from the test sound database unit 10, depending on a test frequency selected by the frequency selection unit 30 and a test sound pressure selected by the sound pressure selection unit 40, and then outputs it through the test sound output unit 50.

Additionally, the test processing unit 80 saves the result of a user's response to a test sound in the test data storage unit 20. For instance, if a user succeeds in hearing a test sound of [1 kHz, 40 dB], the test processing unit 80 saves [1 kHz, −40 dB] in the test data storage unit 20. However, if a user fails in hearing a test sound of [1 kHz, 40 dB], the test processing unit 80 saves [1 kHz, +40 dB] in the test data storage unit 20. Here, a minus sign '−' means that the auditory threshold is present in a region below 40 dB within a test sound pressure zone currently selected, and a plus sign '+' means that the auditory threshold is present in a region above 40 dB.

Also, the test processing unit 80 redefines a test sound pressure zone of a test frequency. Specifically, depending on the result of a user's response to a test sound, the test processing unit 80 divides a test sound pressure zone into an auditory threshold presence region and an auditory threshold absence region on the basis of a test sound pressure. Then, the test processing unit 80 newly selects an auditory threshold presence region as a test sound pressure zone and saves it in the test data storage unit 20.

Figure 7:
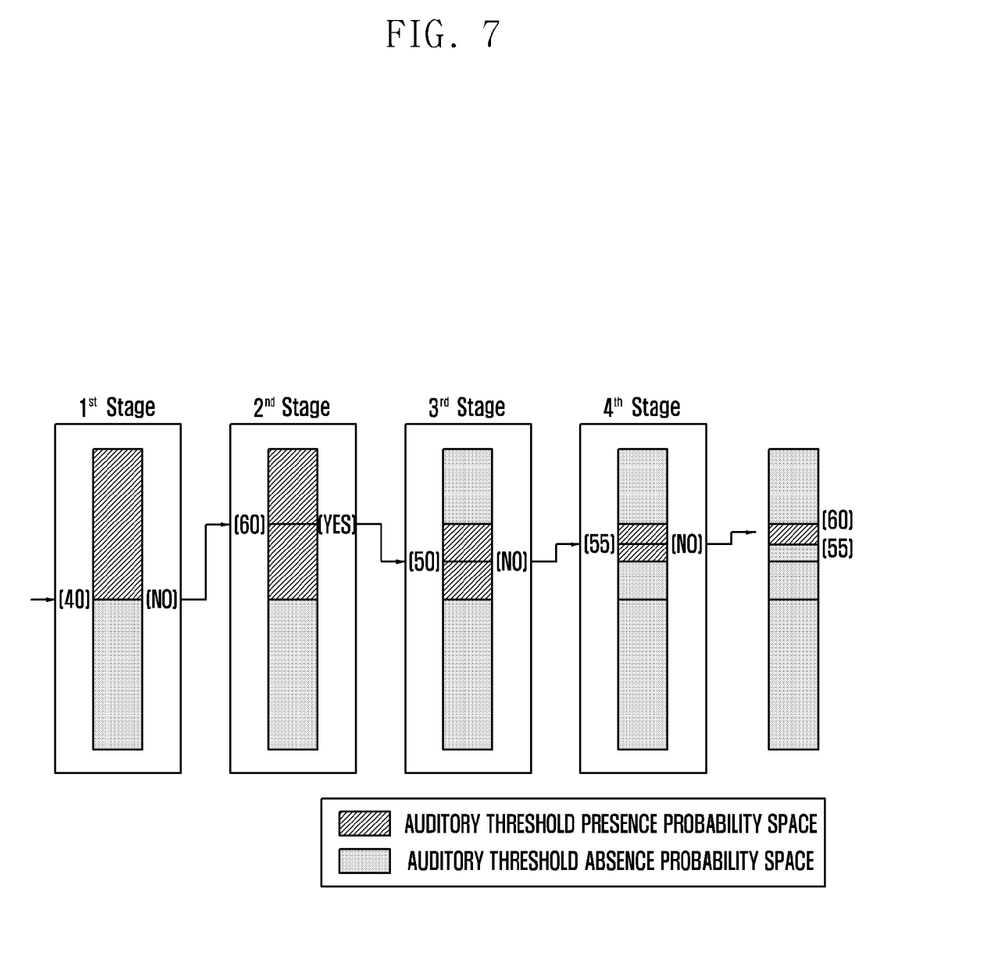
FIGS. 7 and 8 are views illustrating a binary search approach for finding the auditory threshold.
Figure 8:
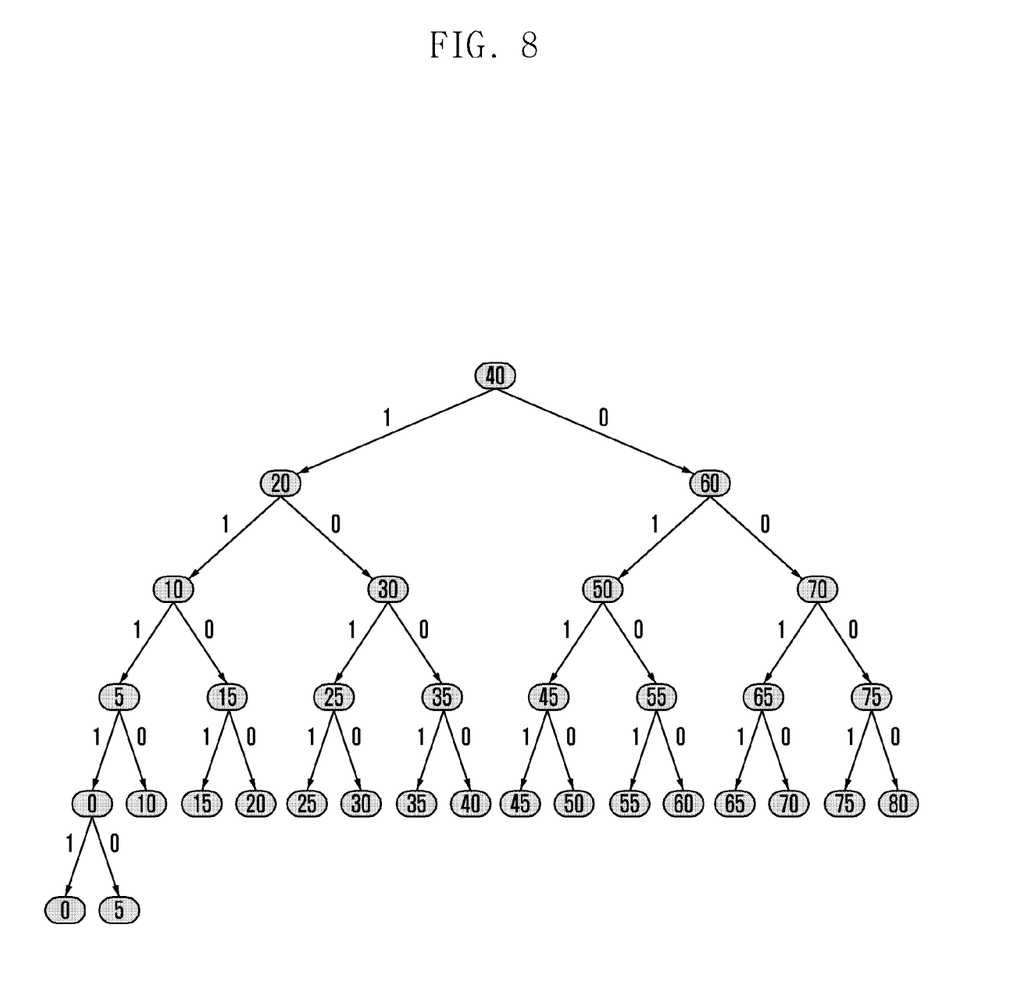

FIGS. 7 and 8 are views illustrating a binary search approach for finding the auditory threshold according to the teachings of the present invention.

The test processing unit 80 repeatedly performs a test for a selected test frequency to find an auditory threshold. This is done by, for example, testing in the middle of frequency in the first stage, and if the response is no, the middle of frequency of the upper zone defined in the first stage is tested in the second stage. If the response is yes in the second stage, the middle of frequency between the first stage and the second stage is tested in the third stage, and so on. If a test is performed four times as shown in FIG. 7 and thereby an auditory threshold presence region, i.e., a probability space in which the auditory threshold will be present, is reduced to 5 dB or less, the test processing unit 80 stops a binary search process and determines the final region as the auditory threshold of a selected test frequency. Alternatively, the test processing unit 80 performs a test five times as shown in FIG. 8 and stops a binary search process when an auditory threshold presence region is reduced to 2.5 dB or less.

Figure 9:
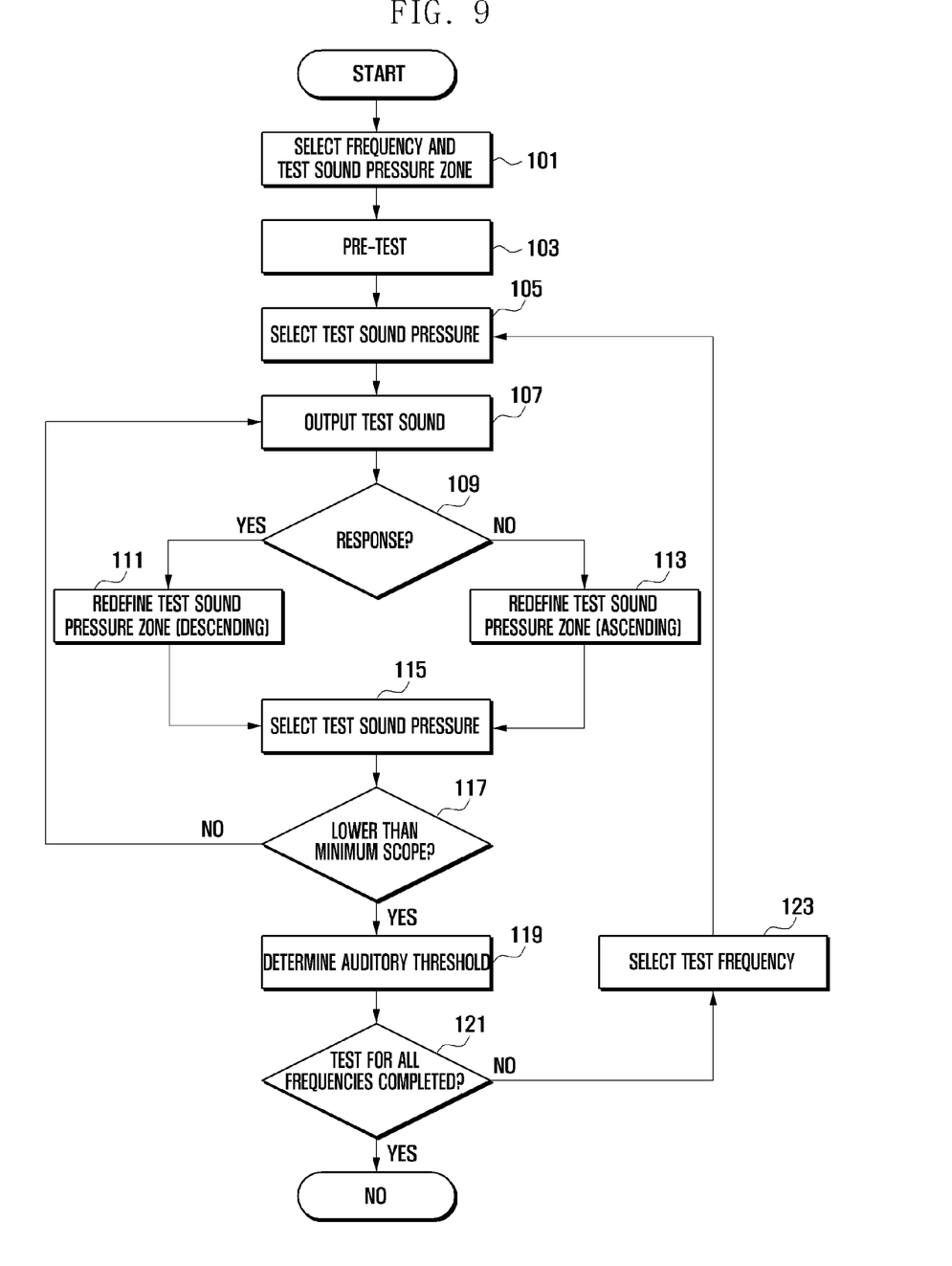
FIG. 9 is a flow diagram illustrating a hearing test method in accordance with an exemplary embodiment of the present invention.

FIG. 9 is a flow diagram illustrating a hearing test method in accordance with an exemplary embodiment of the present invention.

In step 101, the control unit 90 selects specific hearing test frequencies and a test sound pressure zone in response to a user's request for a hearing test. For instance, the hearing test frequency may be selected as 250 Hz, 500 Hz, 1 kHz, 2 kHz, 4 kHz and 8 kHz, and the test sound pressure zone may be selected as [0 dB, 80 dB].

Next, in step 103, when receiving a user's request for a test start, the control unit 90 performs a pre-test before the main test.

The pre-test is performed as follows. The control unit 90 sets a test sound pressure to (0+80)/2=40 dB, controls the test sound output unit 50 to output a test sound of 40 dB at 1-second intervals for each test frequency, and then saves the user response results in the test data storage unit 20. For instance, a user may respond to a test sound of 40 dB for each test frequency, as follows: (250 Hz, 40 dB)=NO, (500 Hz, 40 dB)=YES, (1 kHz, 40 dB)=YES, (2 kHz, 40 dB)=YES, (4 kHz, 40 dB)=NO, (8 kHz, 40 dB)=NO. Here, 'YES' means that a user succeeds in hearing a test sound, and 'NO' means that a user fails to hear the test sound. Next, the control unit 90 redefines a test sound pressure zone for each test frequency and saves it in the test data storage unit 20. For example, if (250 Hz, 40 dB)=NO, the control unit 90 redefines the test sound pressure zone for 250 Hz as a region [40 dB, 80 dB]. Then, the control unit 90 selects an initial test frequency for the main test. For example, the control unit 90 may randomly select the initial test frequency among the hearing test frequencies.

After the pre-test, the main test is performed as follows. In step 105, the control unit 90 selects a test sound pressure. Specifically, the control unit 90 checks a test sound pressure zone for a selected test frequency in the test data storage unit 20. Then, the control unit 90 selects a middle point of a test sound pressure zone as a test sound pressure. For instance, since a test sound pressure zone is currently defined as [40 dB, 80 dB] according to the result of the pre-test in case of a test frequency of 250 Hz, the control unit 90 selects a middle point 60 dB as a test sound pressure.

Next, in step 107, the control unit 90 controls the test sound output unit 50 to output a test sound relevant to selected test frequency and test sound pressure.

Next, in step 109, the control unit 90 determines whether a user responds to a test sound. In an embodiment, if there is a key input/response within one second after the output of a test sound, it is considered as a success in hearing. Otherwise, it is considered as a failure in hearing. In another embodiment, the control unit 90 can specifically asks a user whether he or she succeeds in hearing a test sound, and then receives a key input indicative of success or failure.

On the one hand, if a user responds to a test sound in the step 109, the control unit 90 saves a response result in the test data storage unit 20 and then, in step 111, redefines a test sound pressure zone for a selected test frequency by using a region below a current test sound pressure. For instance, if a user responds to a test sound of [250 Hz, 60 dB], the control unit 90 redefines a test sound pressure zone for 250 Hz as a region [40 dB, 60 dB] below the current test sound pressure.

On the other hand, if a user does not respond to a test sound in the step 109, the control unit 90 saves a response result in the test data storage unit 20 and then, in step 113, redefines a test sound pressure zone for 250 Hz as a region [60 dB, 80 dB] above the current test sound pressure.

Next, in step 115, the control unit 90 selects a test sound pressure of the next test sound. For instance, if a redefined test sound pressure zone is [40 dB, 60 dB], a newly selected test sound pressure is 50 dB. Similarly, if a redefined test sound pressure zone is [60 dB, 80 dB], a newly selected test sound pressure is 70 dB.

Next, in step 117, the control unit 90 determines whether a redefined test sound pressure zone, i.e., a currently selected auditory threshold presence region, is equal to or smaller than a predetermined minimum scope, e.g., 5 dB.

If the redefined test sound pressure zone is greater than a minimum scope 5 dB, the control unit 90 returns to the step 107 and repeatedly performs a binary search process, i.e., the steps 107 to 115.

However, if a redefined test sound pressure zone is equal to or smaller than a minimum scope 5 dB, the control unit 90 proceeds to step 119, determines the redefined test sound pressure zone as the auditory threshold for a selected frequency, and saves it in the test data storage unit 20.

Next, in step 121, the control unit 90 determines whether the auditory thresholds are found for the remaining test frequencies. If the auditory threshold for any test frequency is not found, the control unit 90 selects the next test frequency in step 123 and then returns to the step 105 to perform a test for the next test frequency. Here, the next test frequency may be randomly selected. In some cases, the control unit 90 may preset in advance a random order before a main test and sequentially select frequencies for a test. For instance, the control unit 90 may preset the order of test as 250 Hz, 1 kHz, 8 kHz, 500 Hz, 4 kHz and 2 kHz. In this case, if the auditory threshold for 250 Hz is found, the next frequency to be tested is 1 kHz.

If the auditory thresholds for all test frequencies are found, the control unit 90 ends the entire test process.

Although the above-discussed embodiment shown in FIG. 9 requires a pre-test for respective test frequencies, the pre-test may be omitted in an alternate embodiment.

Figure 10:
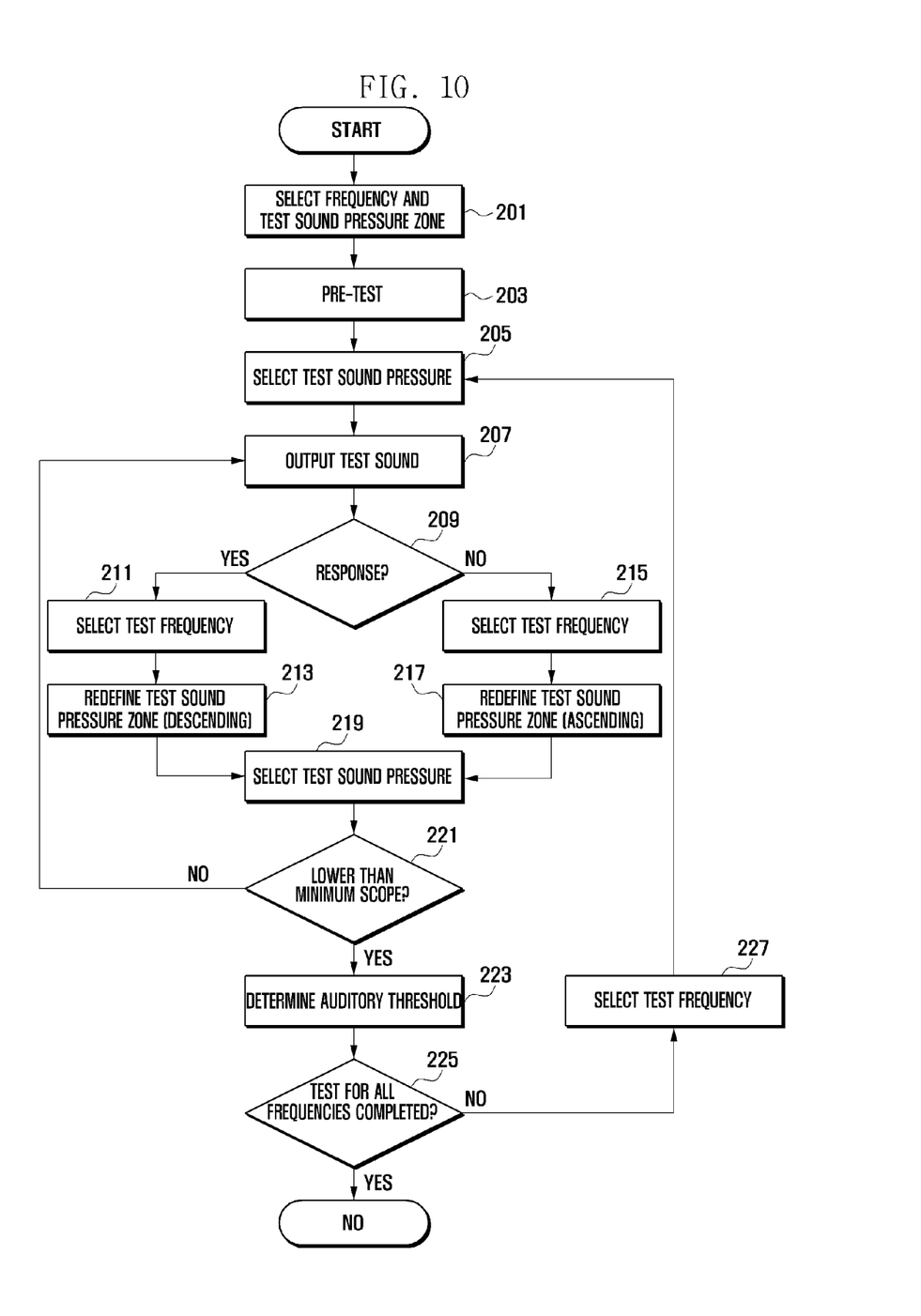
FIG. 10 is a flow diagram illustrating a hearing test method in accordance with another exemplary embodiment of the present invention.

FIG. 10 is a flow diagram illustrating a hearing test method in accordance with another exemplary embodiment of the present invention.

In step 201, the control unit 90 selects specific hearing test frequencies and a test sound pressure zone in response to a user's request for a hearing test.

Next, in step 203, when receiving a user's request for a test start, the control unit 90 performs a pre-test before a main test. Since a pre-test has been described above, the repetition of the same description with reference to FIG. 9 will be avoided herein to avoid redundancy.

After the pre-test, the main test is performed. In step 205, the control unit 90 selects a test sound pressure.

Next, in step 207, the control unit 90 controls the test sound output unit 50 to output a test sound relevant to selected test frequency and test sound pressure.

Next, in step 209, the control unit 90 determines whether a user responds to a test sound.

If a user responds to a test sound in the step 209, the control unit 90 performs steps 211 and 213. In the step 211, the control unit 90 randomly selects the frequency of a test sound to be outputted. Specifically, excepting test frequencies for which the auditory thresholds are determined, the control unit 90 randomly selects one of the rest frequencies. Furthermore, in the step 213, the control unit 90 saves the result of a user's response to a test sound in the test data storage unit 20 and then redefines a test sound pressure zone for a selected test frequency by using a region below a current test sound pressure.

On the other hand, if a user does not respond to a test sound in the step 209, the control unit 90 performs steps 215 and 217. In the step 215, the control unit 90 randomly selects the frequency of a test sound to be outputted. Here, test frequencies for which the auditory thresholds are determined are excluded from selection. Furthermore, in the step 217, the control unit 90 saves the result of a user's response to a test sound in the test data storage unit 20 and then redefines a test sound pressure zone for a selected test frequency by using a region above a current test sound pressure.

Next, in step 219, the control unit 90 selects, as a test sound pressure, a middle point of a test sound pressure zone currently defined for a test frequency selected in the step 211 or 215.

Next, in step 221, the control unit 90 determines whether a test sound pressure zone, i.e., an auditory threshold presence region, currently defined for a test frequency selected in the step 211 or 215 is equal to or smaller than a predetermined minimum scope, e.g., 5 dB.

If a test sound pressure zone is greater than a minimum scope 5 dB, the control unit 90 returns to the step 207 and repeatedly performs a binary search process for a test frequency selected in the step 211 or 215.

However, if a test sound pressure zone is equal to or smaller than a minimum scope 5 dB, the control unit 90 proceeds to step 223, determines a currently defined test sound pressure zone as the auditory threshold for a test frequency selected in the step 211 or 215, and saves it in the test data storage unit 20. For instance, if a test sound pressure zone currently defined for 1 kHz is [55 dB, 60 dB], the auditory threshold for 1 kHz is 57.5±2.5 dB. Namely, a test sound pressure selected in the step 219 is determined as the auditory threshold.

Next, in step 225, the control unit 90 determines whether the auditory thresholds are found for the remaining test frequencies.

If the auditory thresholds for all test frequencies are found, the control unit 90 ends the entire test process.

However, if the auditory threshold for any test frequency is not found, the control unit 90 randomly selects the next test frequency in step 227 and then returns to the step 205 to perform a test for the next test frequency. Here, test frequencies for which the auditory thresholds are determined are excluded from selection.

Although the above-discussed embodiment shown in FIG. 10 requires a pre-test for respective test frequencies, the present invention is not limited to this embodiment. In an alternative embodiment, no pre-test may be needed.

The former embodiment shown in FIG. 9 is to change a test frequency after determining the auditory threshold, whereas the latter embodiment shown in FIG. 10 is to randomly change a test frequency regardless of determination of the auditory threshold. Since the embodiment in case of FIG. 10 always changes a test frequency as well as a test sound pressure, it is more effective in preventing a prediction for the next test sound in comparison with conventional techniques and the embodiment in case of FIG. 9.

TABLE 1

| Measuring method | | Number of test sounds (worst case) | Test time uniformity | Test time (left & right ears) | Accuracy |
|---|---|---|---|---|---|
| Ascending Approach | Increase from lower level | 204 | X | 4 min 45 sec | 5 dB |
| Descending Approach | Decrease from higher level | 204 | X | 4 min 45 sec | 5 dB |
| Mixed Approach | Descend after ascend or vice versa | 408 | ○ | 9 min 30 sec | 5 dB |
| uHear (Apple App) | Ascend after descend | 132 | ○ | 6 min 40 sec | 5 dB |
| Grouping | Configure test sound sets | 204 | X | 3 min 30 sec | 2.5 dB |
| Invention | Reduce auditory threshold presence probability space by half | 48 | ○ | 1 min 7 sec | 2.5 dB |

Table 1 shows experimental results of the present invention and conventional techniques under the same experimental conditions. Test frequencies are composed of 250 Hz, 500 Hz, 1 kHz, 2 kHz, 4 kHz and 8 kHz, and a test sound pressure zone is defined as 0-80 dB. Additionally, test sounds are outputted at 1-second intervals in order to give a user enough time to respond.

As shown in Table 1, the invention is very effective in simultaneously improving both a test time and accuracy that are critical factors in a hearing test. Especially, a test time of this invention is considerably reduced as compared with the grouping approach having the shortest test time among conventional techniques.

Although in the above-discussed embodiments a test sound pressure is set to a middle point in a test sound pressure zone, this is exemplary only and not to be considered as a limitation of the present invention. Alternatively, any other point in a test sound pressure zone may be used as a test sound pressure. For instance, if the entire sound pressure zone is [0 dB, 80 dB] and if the auditory threshold obtained as the result of the prior test is 20 dB, the current test may use 30 dB, as an initial test sound pressure, that is closer to 20 dB than a middle point 40 dB. So then, an auditory threshold presence region initially defined may be probably [0, 30 dB]. Namely, an auditory threshold presence region in this case is much more narrowed than in the above-discussed embodiments. Therefore, this may further increase a test speed. Conditions of determining a test sound pressure may be ambient noises in addition to previous test results.

The above-described methods according to the present invention can be realized in hardware or as software or computer code that can be stored in a recording medium such as a CD ROM, an RAM, a floppy disk, a hard disk, or a magneto-optical disk or downloaded over a network, so that the methods described herein can be executed by such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. A hearing test method comprising:
   (a) selecting a test frequency among a plurality of frequencies for a hearing test;
   (b) selecting a test sound pressure in a test sound pressure zone for the selected test frequency;
   (c) outputting a test sound relevant to the selected test frequency and the selected test sound pressure;
   (d) dividing the test sound pressure zone into an auditory threshold presence region and an auditory threshold absence region according to a user's response to indicate whether the test sound was heard and redefining the test sound pressure zone to correspond to the auditory threshold presence region; and
   (e) determining an auditory threshold for the selected test frequency by repeating step (d) using the redefined test sound pressure zone.

2. The method of claim 1, wherein the redefining of the test sound pressure zone includes:
   if a user succeeds in hearing the test sound, determining a region below the selected test sound pressure as the auditory threshold presence region; and
   if a user fails to hear the test sound, determining a region above the selected test sound pressure as the auditory threshold presence region.

3. The method of claim 2, wherein the auditory threshold presence region is determined as the auditory threshold when equal to or smaller than a predetermined minimum value, and is used to redefine the test sound pressure zone when greater than the predetermined minimum value.

4. The method of claim 2, wherein the selected test sound pressure is a middle point in the test sound pressure zone.

5. The method of claim 1, wherein the test frequency is randomly selected among the plurality of frequencies for the hearing test.

6. The method of claim 5, wherein the order of a random selection for the frequencies is predefined.

7. A hearing test method comprising:
   providing a pre-test for defining a test sound pressure zone for each of a plurality of frequencies for a hearing test; and providing a main test for finding an auditory threshold for each of the plurality of frequencies, wherein the main test includes:
(a) selecting a test frequency among the plurality of frequencies;
(b) selecting a test sound pressure in the test sound pressure zone for the selected test frequency;
(c) outputting a test sound relevant to the selected test frequency and the selected test sound pressure;
(d) dividing the test sound pressure zone into an auditory threshold presence region and an auditory threshold absence region according to a user's response to indicate whether the test sound was heard and redefining the test sound pressure zone to correspond to the auditory threshold presence region; and
(e) determining the auditory threshold for the selected test frequency by repeating step (d) using the redefined test sound pressure zone.

8. The method of claim 7, wherein the test frequency in the main test is randomly selected among the plurality of frequencies for the hearing test.

9. The method of claim 8, wherein the main test further includes selecting other test frequency after the determining of the auditory threshold for the selected test frequency.

10. The method of claim 8, wherein the selecting of the test frequency in the main test includes randomly selecting the test frequency among the remaining frequencies.

11. A hearing test apparatus comprising:
an input unit comprising one or more of a keypad, touch pad, touch screen or microphone;
a control unit comprising a processor configured for executing code to perform a pre-test and a main test, said control unit configuration includes a frequency selection unit configured to select a test frequency among a plurality of frequencies for a hearing test, and a sound pressure selection unit configured to select a test sound pressure in a test sound pressure zone for the selected test frequency;
a test sound output unit comprising a digital to analog converter configured to receive a test sound signal output from the control unit and configured to convert the test sound signal into an analog signal configured to be output as the test sound relevant to the selected test frequency and the selected test sound pressure, and the test sound output unit includes one or more of a speaker, receiver or earphone configured to receive the analog signal and to output the test sound at the selected test frequency and test sound pressure;
wherein the input unit is configured to receive a response to indicate whether a user's response to indicate whether the test sound was heard, and
wherein the control unit further includes a test processing unit configured to determine whether a user hears the test sound as indicated from an input received by the input unit, to divide the test sound pressure zone into an auditory threshold presence region and an auditory threshold absence region, to redefine the test sound pressure zone to correspond to the auditory threshold presence region, and to determine an auditory threshold for the selected test frequency through a repeated redefining of the test sound pressure zone.

12. The apparatus of claim 11, wherein the test processing unit is further configured to determine a region below the selected test sound pressure as the auditory threshold presence region if a user succeeds in hearing the test sound.

13. The apparatus of claim 12, wherein the test processing unit is further configured to determine a region above the selected test sound pressure as the auditory threshold presence region when the input unit indicates a user fails to hear the test sound.

14. The apparatus of claim 13, wherein the test processing unit is further configured to determine the auditory threshold presence region as the auditory threshold if the auditory threshold presence region is equal to or smaller than a predetermined minimum value.

15. The apparatus of claim 14, wherein the test processing unit is further configured to use the auditory threshold presence region to redefine the test sound pressure zone if the auditory threshold presence region is greater than the predetermined minimum value.

16. The apparatus of claim 15, wherein the sound pressure selection unit is further configured to select a predetermined point in the test sound pressure zone as the test sound pressure.

17. The apparatus of claim 16, wherein the sound pressure selection unit is further configured to randomly select the test frequency among the plurality of frequencies for the hearing test.

18. The apparatus of claim 17, further comprising a non-transitory test data storage unit configured to store the auditory threshold.

* * * * *